United States Patent [19]

Sugiyama et al.

[11] Patent Number: 5,225,587

[45] Date of Patent: Jul. 6, 1993

[54] METHOD OF PRODUCING α-L-ASPARTYL-L-PHENYLALANINE METHYL ESTER HYDROCHLORIDE

[75] Inventors: Katsumi Sugiyama, Yokkaichi; Kiyo Adachi; Toshihide Yukawa, both of Kawasaki, all of Japan

[73] Assignee: Ajinomoto Co., Inc., Tokyo, Japan

[21] Appl. No.: 864,133

[22] Filed: Apr. 6, 1992

Related U.S. Application Data

[63] Continuation of Ser. No. 633,183, Dec. 28, 1990, abandoned, which is a continuation of Ser. No. 129,177, Dec. 7, 1987, abandoned, which is a continuation of Ser. No. 874,391, Jun. 16, 1986, abandoned.

[30] Foreign Application Priority Data

Jul. 12, 1985 [JP] Japan .................. 63-153645

[51] Int. Cl.$^5$ ............................. C07C 103/52
[52] U.S. Cl. ............................. 560/41
[58] Field of Search .......................... 560/41

[56] References Cited

U.S. PATENT DOCUMENTS 3,798,207  3/1974  Ariyoshi et al. ............... 560/41

Primary Examiner—Arthur C. Prescott
Attorney, Agent, or Firm—Oblon, Spivak, McClelland, Maier & Neustadt

[57] ABSTRACT

A method of purifying α-L-aspartyl-L-phenylalanine methyl ester as a hydrochloride salt thereof which comprises:
i) contacting a mixture of α-L-aspartyl-L-phenylanaline methyl ester and β-L-aspartyl-L-phenylalanine methyl ester with an aqueous medium containing (a) hydrogen chloride in an amount not more than ca. 2 mol., per liter of said aqueous medium, but not less than 1 mol., per mole of said of said mixture of α-L-aspartyl-L-phenylalanine methyl ester and β-L-aspartyl-L-phenylalanine methyl ester, and (b) an inorganic chloride selected from the group consisting of NaCl, KCl, NH$_4$Cl, CaCl$_2$, and ZnCl$_2$ in an amount of at least ca. 50 g., per liter of said aqueous medium, to form crystals of α-L-aspartyl-L-phenylalanine methyl ester hydrochloride, and
ii) recovering the α-L-aspartyl-L-phenylalanine methyl ester hydrochloride crystals therefrom.

4 Claims, 2 Drawing Sheets

METHOD OF PRODUCING α-L-ASPARTYL-L-PHENYLALANINE METHYL ESTER HYDROCHLORIDE

This application is a continuation of application Ser. No. 07/633,183, filed Dec. 28, 1990, which is a continuation of Ser. No. 07/129,177, filed Dec. 7, 1987, which is a continuation of Ser. No. 06/874,391, filed Jun. 16, 1986 now abandoned.

DETAILED DESCRIPTION OF THE INVENTION

The present invention relates to a method of producing α-L-aspartyl-L-phenylalanine methyl ester hydrochloride.

α-L-aspartyl-L-phenylalanine methyl ester (hereinafter referred to as α-APM) is a substance which has been attracting a wide attention for its usefulness as a sweetening agent with a low calorie and a sweeteness of excellent quality.

In known methods for producing α-AMP, an N-protected-L-aspartic anhydride is reacted with L-phenylalanine methyl ester in an organic solvent, and then the protecting group is eliminated by a conventional method (U.S. Pat. No. 3,786,039); and addition salt of L-aspartic anhydride with a strong acid is directly reacted with L-phenylalanine methyl ester (Japanese Patent Publication No. 14,217/74); or L-phenylalanine is reacted with N-formyl-L-aspartic anhydride in glacial acetic acid, and the formyl group is eliminated from the product to give α-L-aspartyl-L-phenylalanine (hereinafter referred to as α-AP), which is then esterified with methanol (U.S. Pat. No. 3,933,781).

In the known methods, however, β-isomers of the desired α-derivatives, such as α-APM and α-AP, are formed as a by-product in large quantities. In addition, unreacted starting materials (for example, derivatives of L-aspartic acid and L-phenylalanine) also remain in the reaction mixture. It is, therefor, of vital importance in a commercial production of α-APM to isolate and purify α-APM from a reaction mixture containing such impurities in an efficient manner.

In a known purification method, α-APM contaminated with β-L-aspartyl-L-phenylalanine methyl ester (hereinafter referred to as β-APM) and other impurities is brought into contact with a hydrogen halide (for example, hydrogen chloride) in water or in an aqueous medium comprising water and methanol in order to precipitate crystals of the salt of the hydrogen halide and α-APM, and the crystals precipitated are then separated therefrom (U.S. Pat. No. 3,798,207).

In an improvement of the method described in U.S. Pat. No. 3,933,781, α-AP is contacted with a reaction mixture containing methanol, a hydrogen halide and water, so as to convert the α-AP into α-APM, which precipitates immediately in the form of a salt with the hydrogen halide (U.S. Pat. No. 4,173,562).

The above-described known methods, which comprise precipitating crystals of a hydrogen halide salt of α-APM, can be useful in enhancing the efficiency in its commercial production since they make it possible to convert α-AP into α-APM and/or to separate and purify α-APM quite efficiently. However, in order to precipitate the salt of α-APM in a high yield, said precipitation must be carried out in the presence of a large excess of hydrogen halides. For example, hydrogen halides must be used in an excess of not less than ca. 2 mol., preferably not less than ca. 3 mol., per liter of the aqueous medium, as is clearly indicated by the solubility curves shown in FIG. 1. The methods, therefore, suffers from the disadvantages that α-APM could hardly be produced in a high yield since the ester and peptide bonds contained in its molecule are subjected to hydrolysis and that a large quantity of alkali is required to neutralize the excess hydrogen halides. In addition, hydrogen halides are highly corrosive to ordinary metals and, therefore, a reaction equipment made of high-quality materials must be used in a commercial scale production of α-APM. This requires an undesirably high cost for equipment.

The inventors have conducted intensive investigations for the purpose of overcoming the above disadvantages, thereby using hydrochloric acid as a hydrohalogenic acid for a commercial scale production. As a result, it has been found that α-APM hydrochloride can be efficiently precipitated out of an aqueous medium by carrying out its precipitation in the presence of more than a certain amount of inorganic chlorides, even when hydrogen chloride is used in a considerably decreased quantity. The present invention has been accomplished based on the above finding.

The invention is concerned with a method of producing α-APM hydrochloride which comprises, upon precipitation of α-APM out of an aqueous medium, bringing it into contact with a considerably decreased quantity of hydrogen chloride in an aqueous medium in the presence of an inorganic halide.

According to the invention, there is provided a method of producing α-APM hydrochloride which is free from the above-described disadvantages with regard to its commercial production, wherein (i) α-APM hydrochloride is precipitated by bringing α-APM into contact with a low concentration of hydrogen chloride in an aqueous medium in the presence of an inorganic chloride, or (ii) α-APM is brought into contact with methanol and a low concentration of hydrogen chloride in an aqueous medium in the presence of an inorganic halide, thus allowing α-APM formed in accordance with the following equilibrium:

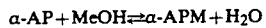

$$\alpha\text{-AP} + \text{MeOH} \rightleftharpoons \alpha\text{-APM} + \text{H}_2\text{O}$$

to precipitate immediately in the form of a hydrochloride salt.

The concentration of hydrogen chloride to be used in the invention can be decided by experiments, taking into consideration its corrosiveness to the materials, in particular, metals used for the reaction equipment to be employed, as well as the hydrolysis of the ester and peptide bonds contained in α-APM.

The inventors have conducted extensive investigations on the influence of the concentration of hydrogen chloride in the method according to the invention. The investigations, however, have been conducted only at temperatures not higher than 30° C. in view of the poor thermal stability of α-APM, in particular, under highly acidic conditions as is the case of the method according to the invention.) As a result, it has been proved, as shown in Tables 1 and 2, that the adverse effects can be decreased to a fairly low level when hydrogen chloride is used in an amount not greater than 2 mol., per liter of the aqueous medium, and almost no adverse effects are caused when it is used in an amount not greater than 1 mol., per liter of the aqueous medium. The method of the present invention, therefore, is practiced in the presence of not more than 2 mol., preferably not more than 1 mol., of hydrogen chloride, per liter of the aqueous medium.

TABLE 1

| Material of Test Piece | Temperature | Test Time | Attacking Rate (mm./year) HCl Contained in Dipping Solution (*) (Mol./l.) | | |
|---|---|---|---|---|---|
| | | | 1 | 2 | 3 |
| 316 SS | 30° C. | 100 hrs. | 0.0050 | 0.012 | 0.13 |
| Modified 317SS | do | do | 0.0015 | 0.0085 | 0.11 |
| Ti | do | do | 0.0017 | 0.0075 | 0.082 |

(Note) (*): In the dipping solutions were additionally incorporated 10 g./l. (initial concentration) of α-APM and 10 g./l. (initial concentration) of β-APM.

TABLE 2

| Concentration of HCl (Mol./l.) | Percentage (%) of α-APM Decomposed in 7 hours (*) | |
|---|---|---|
| | 5° C. | 25° C. |
| 1 | 0.7% | 2.4% |
| 2 | 2.1% | 7.5% |
| 3.5 | 7.6% | 32.7% |

(Note) (*): Initial concentration of α-APM was 10 g./l.

In the method according to the invention, there can be used any inorganic halide which is soluble in an amount not smaller than ca. 50 g., per liter of the aqueous medium and does not hinder the precipitation of α-APM hydrochloride, as exemplified by NaCl, KCl, NH$_4$Cl, CaCl$_2$, ZnCl$_2$, and the like. In order to precipitate α-APM hydrochloride efficiently, the concentration of the inorganic salt must be above a certain level, which depends on the concentration of hydrogen chloride. In general, a concentration higher than the level can be preferred.

The required concentration of the inorganic chloride varies to some extent, depending on the kind of inorganic halides used. As shown in FIG. 2, however, the inorganic halides can be used with advantage in an amount not lower than ca. 50 g., per liter of the aqueous medium with concentrations of hydrogen chloride of from 1 mol. to 2 mol., per liter of the aqueous medium. In aqueous solutions containing hydrogen chloride in relatively low concentrations, i.e., in concentrations up to 1 mol., per liter of the aqueous medium, the inorganic halides can be used with advantage in an amount not smaller than ca. 100 g. It is a matter of course that the inorganic halides are to be used in concentrations at which no precipitates of the halides are generated.

An inorganic halide-containing aqueous medium can be prepared by adding an crystalline inorganic halide or an aqueous solution of an inorganic halide to an aqueous medium, or by neutralizing hydrogen chloride contained in an aqueous medium with a solution of such metal hydroxides as NaOH, KOH, Ca(OH)$_2$ and Zn(OH)$_2$, or aqueous ammonia, thereby forming an inorganic chloride in situ. It is also possible to use an inorganic chloride formed as a by-product in a commercial production process.

In the method according to the invention, there can be used a solvent consisting of water alone, as well as a mixture of methanol and water. The solvent used in the invention can be additionally admixed with other solvents which do not hinder the addition reaction between α-APM and hydrogen chloride, such as ethanol, ethylene glycol and acetone, in an amount not reducing the solubility of the inorganic halides to an extremely low level.

In the method according to the invention, α-AP is brought into contact with methanol in the presence of methanol, in order to immediately precipitate the addition salt formed in situ from α-APM and hydrogen chloride. The present inventors have conducted further investigations on the amount of methanol to be contained in the aqueous medium and, as a result, found that α-AP can be efficiently converted into α-APM hydrochloride even when methanol is contained in the aqueous medium in a relatively low concentration.

When methanol is used, it was also found, in an unnecessarily large amount, α-APM formed by the conversion tends to be further esterified to give a derivative in which the β-carboxyl group contained in the aspartic residue is esterified with methanol (hereinafter referred to as α-A(M)PM), in a markedly increased amount, thus resulting in a significant reduction in the conversion from α-AP into α-APM. On the other hand, if the amount of methanol used is reduced too much, a decreased rate of conversion from α-AP into α-APM will be resulted, although it could be advantageous in preventing the undesirable side reaction from α-APM into α-A(M)PM.

In view of the above, the inventors have conducted investigations on the amount of methanol to be used for the conversion from α-AP into α-APM according to the invention. As a result, it has been proved, as shown in Example 6, that the most effective amount of methanol is in the range of from ca. 0.5 mol. to ca. 2 mol., per liter of the reaction medium, or the aqueous solvent.

Accordingly, it can be advantageous, in the case where the methanol contained in a reaction medium is consumed through the esterification of α-AP and its concentration is reduced to a level below the lower limit of the above range, to add an additional methanol to the reaction mixture in the course of the reaction. When all methanol used for the reaction is allowed to be present in the reaction mixture from the beginning of the reaction, an undesirable increase in the formation of α-A(M)PM may be resulted. It would be needless to say that at least 1 mol., in total, of methanol is required to convert 1 mol. of α-AP into α-APM.

The present invention will further be illustrated by way of examples.

EXAMPLE 1

Into 1,000 ml. of 2N hydrochloric acid was dissolved 25 g. of α-APM at 40° C., and the resulting solution was divided into three equal portions, each of which was then placed separately in 500 ml. of flasks equipped with a stirrer. One flask was set on a water bath maintained at 5° C. and stirred overnight to effect precipitation (Case A). To the solutions placed in the other flasks was added 3.3 g. (Case B) or 16.7 g. (Case C) of sodium chloride, and the sodium salt was dissolved. The flasks were then treated under the same conditions as in Case A.

The crystals precipitated were filtered off, washed with small portions of cold 2N hydrochloric acid, and then vacuum dried at 50° C. The crystals obtained in either case gave infrared spectra identical with that of an authentic α-APM and had a purity of 98% or above (determined by chromatography). Results obtained are shown in Table 3.

TABLE 3

| Case | NaCl (g.) | α-APM Hydrochloride Yielded (g.) | α-APM Hydrochloride Yielded (%) |
|---|---|---|---|
| A | 0 | 7.1 | 67 |
| B | 3.3 | 7.3 | 69 |
| C | 16.7 | 9.4 | 89 |

Note: In this example, Cases A and B are controls.

EXAMPLE 2

An aqueous solution (495 ml.) containing 15 g. of α-APM and 30 g. of calcium chloride was placed in a 1 liter flask equipped with a stirrer. To the solution was gradually added 105 ml. of 35% hydrochloric acid, and the resulting mixture was stirred overnight, while maintaining its temperature at 5° C.

The crystals precipitated were treated in the same manner as in Example 1 to obtain 17.2 g. of crystals having a purity of 98.7%. Yield: 90.2%.

EXAMPLE 3

In a mixture of 500 ml. of 1.1N hydrochloric acid and 50 ml. of methanol was dissolved 15 g. of α-APM, and the resulting solution was divided into two equal portions. One of the portions was stored overnight in a refrigerator (Case A). On the other hand, 60 g. of ammonium chloride was added to the other portion and dissolved, and then the resulting mixture was stored overnight in a refrigerator (Case B).

The crystals precipitated were treated in the same manner as in Example 1. In case A (control), 6.1 g. of crystals having a purity of 98.2% was obtained, whereas in case B, 8.7 g. of crystals having a purity of 97.6% was obtained (the purities were determined by chromatography). Yields: 64.1% (Case A); 90.8% (Case B).

EXAMPLE 4

In 500 ml. of water was suspended 28 g. of α-APM and 12 g. of β-APM, and the pH of the resulting suspension was adjusted to 2.2 with 35% hydrochloric acid in order to dissolve the suspended substances. The thus obtained solution was then divided into two equal portions. To one of them was added 150 ml. of 35% hydrochloric acid, and the resulting mixture was stirred for 15 hours at 15° C. to effect precipitation (Case A). To the other portion was added 150 ml. of 35% hydrochloric acid. Thereafter, 61 g. of powdered anhydrous sodium carbonate was gradually added to the mixture in order to neutralize part of the excess hydrochloric acid. The resulting mixture was stirred for 15 hours at 15° C. to effect precipitation.

The crystals obtained were treated in the same manner as in Example 1. Results obtained are shown in Table 4. In this example, Case A is a coltrol.

TABLE 4

| Case | Crystals Yielded (g.) | Yield (%) | Impurities Contained in Crystals (%)* β-APM | α-AP | β-AP |
|---|---|---|---|---|---|
| A | 12.3 | 69 | 0 | 0.52 | 0.37 |
| B | 14.9 | 83.5 | 0 | 0.09 | 0.05 |

(Note) *: Determined by amino acid analysis.

In the mother liquids was contained hydrogen chloride in concentrations as set forth below:
A: 4 mol./l.
B: 1.4 mol./l. (NaCl: 150 g./l.).

EXAMPLE 5

In a mixture of 38 ml. of methanol and 900 ml. of 2N hydrochloric acid was dissolved 143 g. of α-AP having a purity of 98.2%, and the resulting solution was divided into two equal portions. One portion was stored with stirring at 25° C. for 3 days and then at 10° C. for 24 hours to precipitate the crystals of α-APM hydrochloride (Case A). To the other portion was added 51 g. of crystals of ammonium chloride. The ammonium chloride was dissolved with stirring and the resulting mixture was treated in the same manner as above (Case B).

The crystals precipitated were treated in the same manner as in Example 1 to give 32.0 g. (Case A) or 62.9 g. (Case B) of crystals. The crystals gave infrared spectra identical with that of an authentic α-APM hydrochloride and had compositions as shown in Table 5 (the compositions were determined by liquid chromatography). In this example, Case A is a control.

TABLE 5

| Case | Purity of α-APM* | Composition (Mol %) α-APM | α-AP | α-A(M)P** | α-A(M)PM | Yield |
|---|---|---|---|---|---|---|
| A | 85.7% | 85 | 8 | 1 | 6 | 29.9% |
| B | 90.3% | 91 | 6 | 1 | 3 | 61.9% |

(Notes)
*: Purity as α-APM HCl 2H₂O methyl ester.
**: Derivative of α-AP in which the β-carboxyl group in the aspartic residue is esterified with methanol.

In this example, the initial concentration of methanol was 0.92 mol./l. and the concentration of NH₄Cl in the mother liquid in Case B was 100 g./l.

EXAMPLE 6

In 1,500 ml. of 1N hydrochloric acid were dissolved 215.6 g. of α-APM having a purity of 97.5% and 200 g. of sodium chloride. The resulting solution was divided into 5 equal portions, and each portion was placed in a four necked flask equipped with a stirrer.

To them was added 5 ml. (Case A), 7 ml. (Case B), 14 ml. (Case C), 30 ml. (Case D) or 50 ml. (Case E) of methanol, and the resulting mixtures were treated in the same manner as in Example 5. Crystals of α-APM hydrochloride were obtained in an amount of 17.5 g. (Case A), 28.6 g. (Case B), 33.3 g. (Case C), 33.0 g. (Case D) or 21.6 g. (Case E).

The compositions of the crystals were analyzed by liquid chromatography. Results obtained are shown in Table 6, together with the yields of α-APM. In this example, Cases A and E are controls. It would be understood that a large quantity of α-AP is formed in the case where the concentration of methanol is low and a large quantity of α-A(M)PM is formed when the concentration of methanol is high.

TABLE 6

| Case | Amount of Methanol (Mol./l.) | Purity of α-APM · HCl* | Composition (Mol %) α-APM | α-AP | α-A(M)P | α-A(M)PM | Yield |
|---|---|---|---|---|---|---|---|
| A | 0.36 | 79.1% | 77 | 22 | 1 | 0 | 25.1% |

TABLE 6-continued

| Case | Amount of Methanol (Mol./l.) | Purity of α-APM · HCl* | Composition (Mol %) | | | | Yield |
|---|---|---|---|---|---|---|---|
| | | | α-APM | α-AP | α-A(M)P | α-A(M)PM | |
| B | 0.50 | 89.0% | 88 | 10 | 1 | 1 | 46.2% |
| C | 0.93 | 90.5% | 91 | 5 | 1 | 3 | 54.7% |
| D | 2.0 | 88.7% | 89 | 4 | 1 | 6 | 53.2% |
| E | 3.2 | 79.8% | 82 | 3 | 1 | 14 | 31.3% |

(Notes)
*: Purity as α-APM.
**: Amount of methanol in the solution just after its addition.

Figure 1:
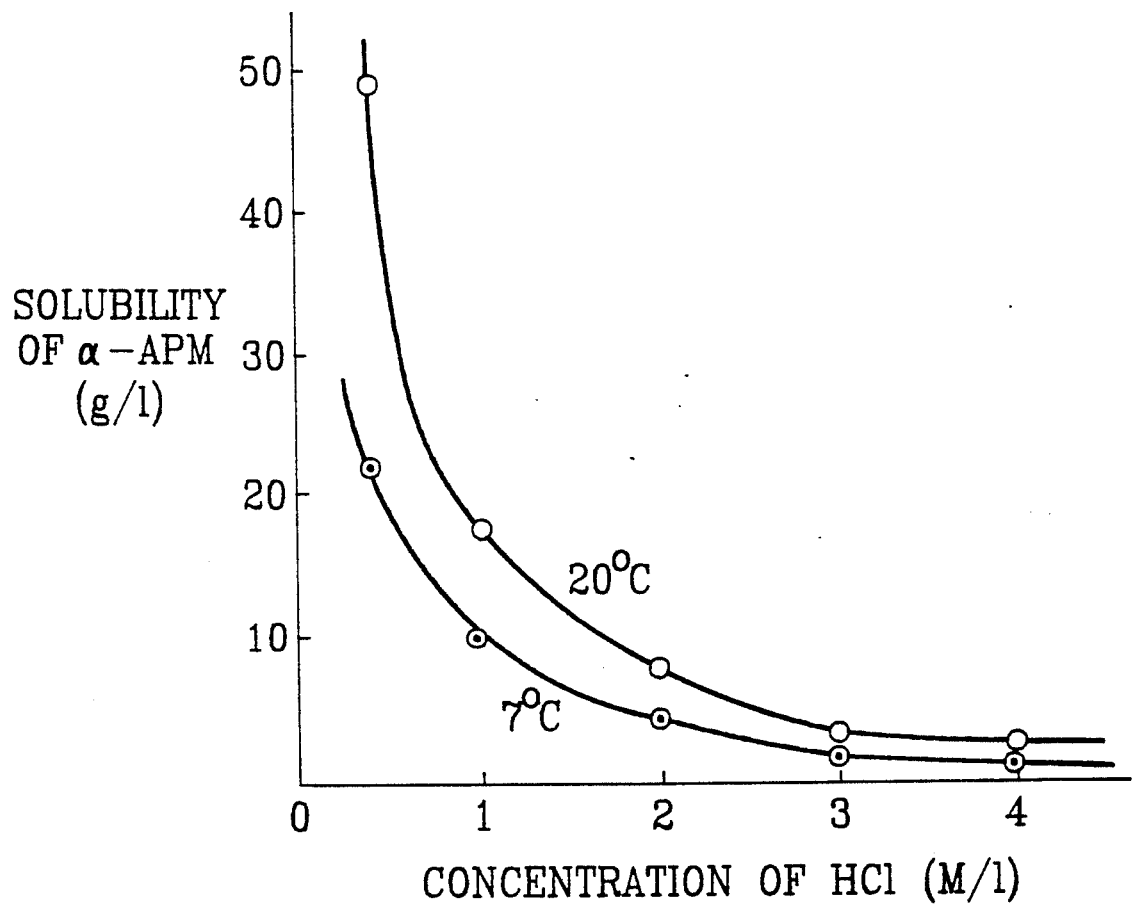
FIG. 1 is a graph showing the relationship between the density of hydrogen chloride and the solubility of α-APM at different temperatures.
Figure 2:
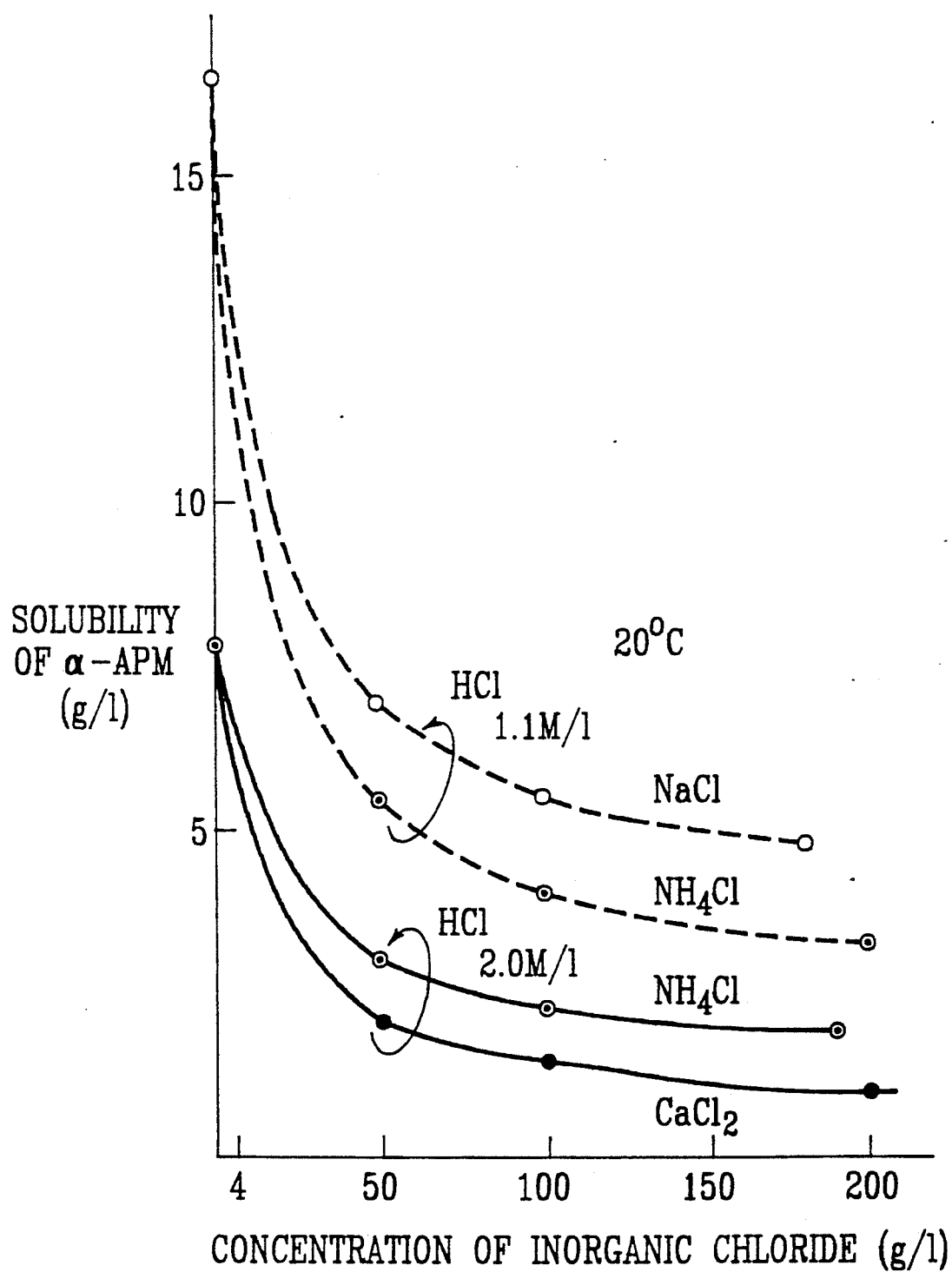
FIG. 2 is a graph showing the relationship between the density of halides and the solubility of α-APM in the presence of different concentrations of hydrogen chloride.

What is claimed is:

1. A method of purifying α-L-aspartyl-L-phenylalanine methyl ester as a hydrochloride salt thereof which comprises:
   i) contacting a mixture of α-L-aspartyl-L-phenylalanine methyl ester and β-L-aspartyl-L-phenylalanine methyl ester with an aqueous medium containing (a) hydrogen chloride in an amount not more than ca. 2 mol., per liter of said aqueous medium, but not less than 1 mol., per mole of said mixture of α-L-aspartyl-L-phenylalanine methyl ester and β-L-aspartyl-L-phenylalanine methyl ester, and (b) an inorganic chloride selected from the group consisting of NaCl, KCl, NH4Cl, CaCl2, and ZnCl2 in an amount of at least ca. 50 g., per liter of said aqueous medium, to form α-L-aspartyl-L-phenylalanine methyl ester hydrochloride crystals, and
   ii) recovering said α-L-aspartyl-L-phenylalanine methyl ester hydrochloride crystals from the aqueous solution containing β-L-aspartyl-L-phenylalanine methyl ester hydrochloride.

2. The method of claim 1, wherein said aqueous medium contains (a) hydrogen chloride in an amount not more than ca. 1 mol., per liter of said aqueous medium, but not less than 1 mol., per mole of said mixture of α-L-aspartyl-L-phenylalanine methyl ester and β-L-aspartyl-L-phenylalanine methyl ester, and (b) an inorganic chloride selected from the group consisting of NaCl, KCl, NH4Cl, CaCl2, and ZnCl2 in an amount not less than ca. 100 g., per liter of said aqueous medium.

3. A method of purifying α-L-aspartyl-L-phenylalanine as the hydrochloride salt of the methyl ester thereof which comprises:
   i) contacting a mixture of α-L-aspartyl-L-phenylalanine and β-L-aspartyl-L-phenylalanine with an aqueous medium containing (a) hydrogen chloride in an amount not more than ca. 2 mol., per liter of said aqueous medium, but not less than 1 mol., per mole of said mixture of α-L-aspartyl-L-phenylalanine and β-L-aspartyl-L-phenylalanine, (b) an inorganic chloride selected from the group consisting of NaCl, KCl, NH4Cl, CaCl2, and ZnCl2 in an amount of at least ca. 50 g., per liter of said aqueous medium, and (c) methanol in an amount not less than 1 mol., per mole of said mixture of α-L-aspartyl-L-phenylalanine and β-L-aspartyl-L-phenylalanine to form α-L-aspartyl-L-phenylalanine methyl ester hydrochloride crystals, and
   ii) recovering said α-L-aspartyl-L-phenylalanine methyl ester hydrochloride crystals from the aqueous solution containing β-L-aspartyl-L-phenylalanine methyl ester hydrochloride.

4. The method of claim 3, wherein said aqueous medium contains (a) hydrogen chloride in an amount not more than ca. 1 mol., per liter of said aqueous medium, but not less than 1 mol., per mole of said mixture of α-L-aspartyl-L-phenylalanine and β-L-aspartyl-L-phenylalanine, (b) an inorganic chloride selected from the group consisting of NaCl, KCl, NH4Cl, CaCl2, and ZnCl2 in an amount not less than ca. 100 g., per liter of said aqueous medium, and (c) methanol in an amount of from ca. 0.5 mol. to ca. 2 mol., per liter of said aqueous medium, but not less than 1 mol., per mole of said mixture of α-L-aspartyl-L-phenylalanine and β-L-aspartyl-L-phenylalanine.

* * * * *